United States Patent [19]

Dulebohn

[11] Patent Number: 5,044,540
[45] Date of Patent: Sep. 3, 1991

[54] SURGICAL STAPLING INSTRUMENT

[75] Inventor: David H. Dulebohn, Tonka Bay, Minn.

[73] Assignee: Micro Precision, Inc., Plymouth, Minn.

[21] Appl. No.: 488,319

[22] Filed: Mar. 5, 1990

[51] Int. Cl.⁵ .............................................. B31B 1/00
[52] U.S. Cl. ...................................... 227/175; 227/19
[58] Field of Search ..................... 227/19, 82, 83, 156, 227/175; 72/409, 410; 128/334 R, 325, 335, 346

[56] References Cited

U.S. PATENT DOCUMENTS

| | | | |
|---|---|---|---|
| 4,396,139 | 8/1983 | Hall et al. | 227/19 |
| 4,526,174 | 7/1985 | Froehlich | 227/19 X |
| 4,550,870 | 11/1985 | Krumme et al. | 227/19 |
| 4,619,262 | 10/1986 | Taylor | 227/19 X |
| 4,762,260 | 8/1988 | Richards et al. | 227/19 |

Primary Examiner—Timothy V. Eley
Attorney, Agent, or Firm—Kinney & Lange

[57] ABSTRACT

An instrument for stapling body tissue including a staple, a retainer, and a plunger. The staple is preformed in a closed state and is made of a body-compatible material. The staple material has a stress plateau such that the staple may be flexed to an open state without permanent deformation. The retainer stores the staple in the open state and the plunger ejects the staple from the retainer such that the staple returns itself to the preformed closed state in the body tissue.

18 Claims, 2 Drawing Sheets

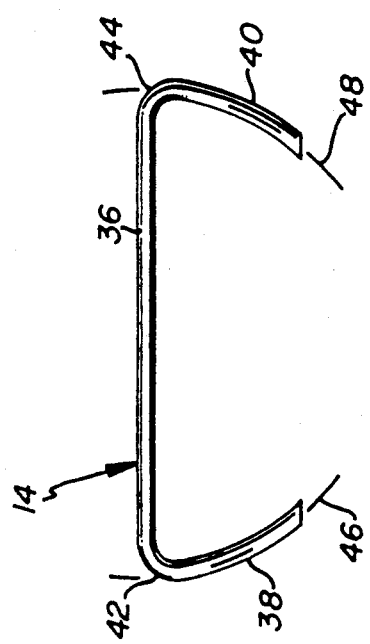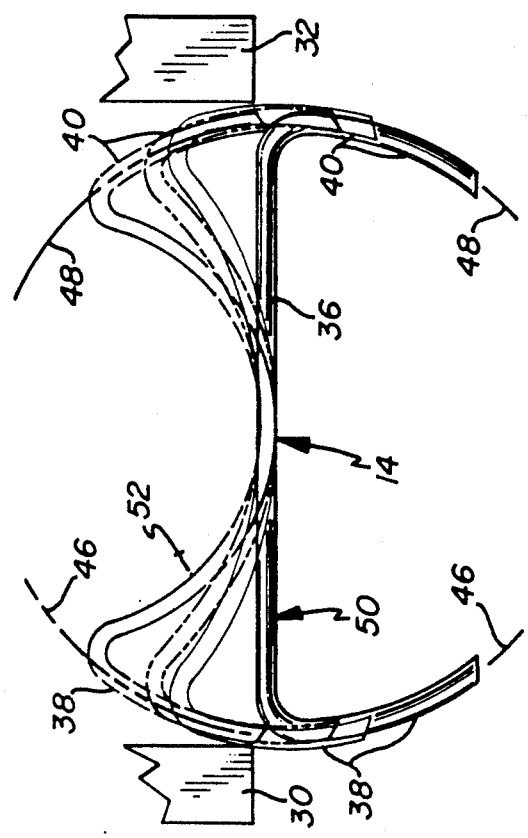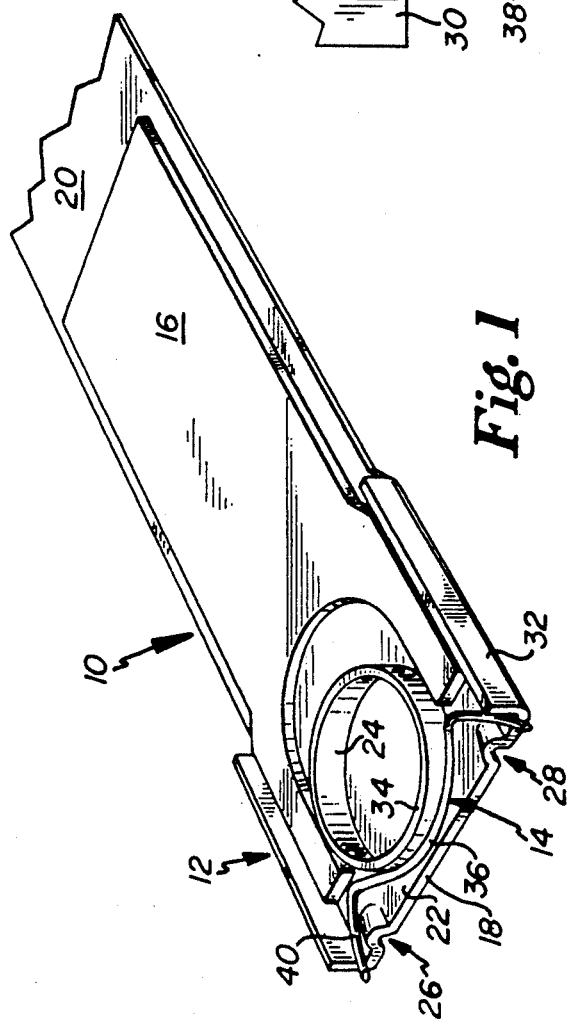

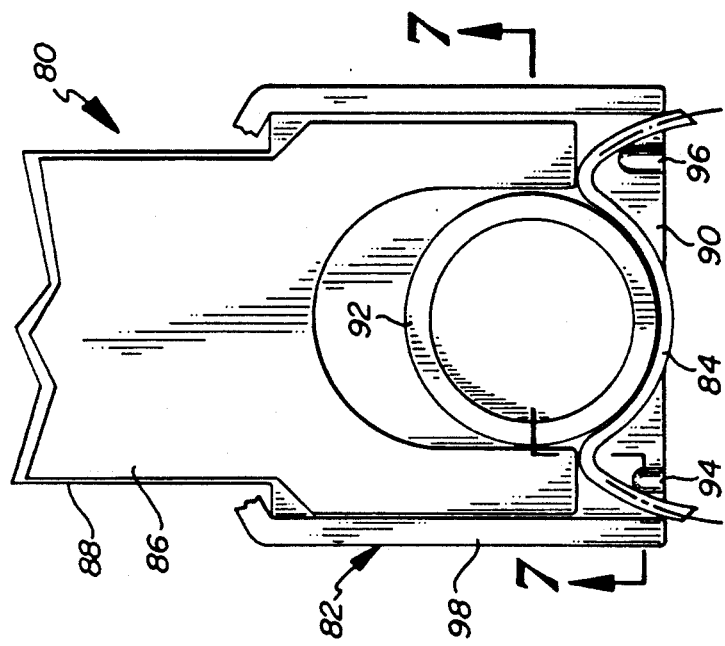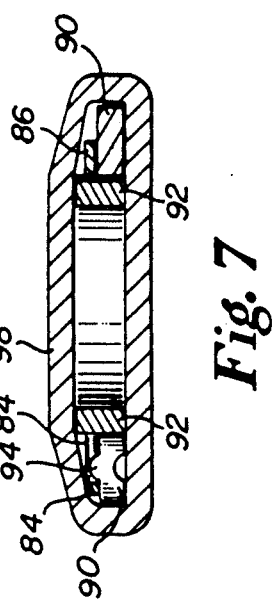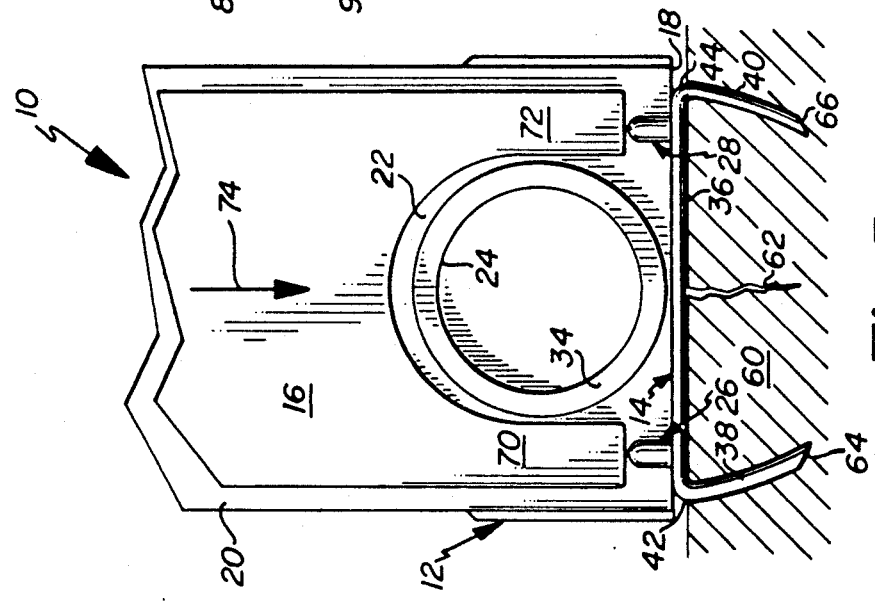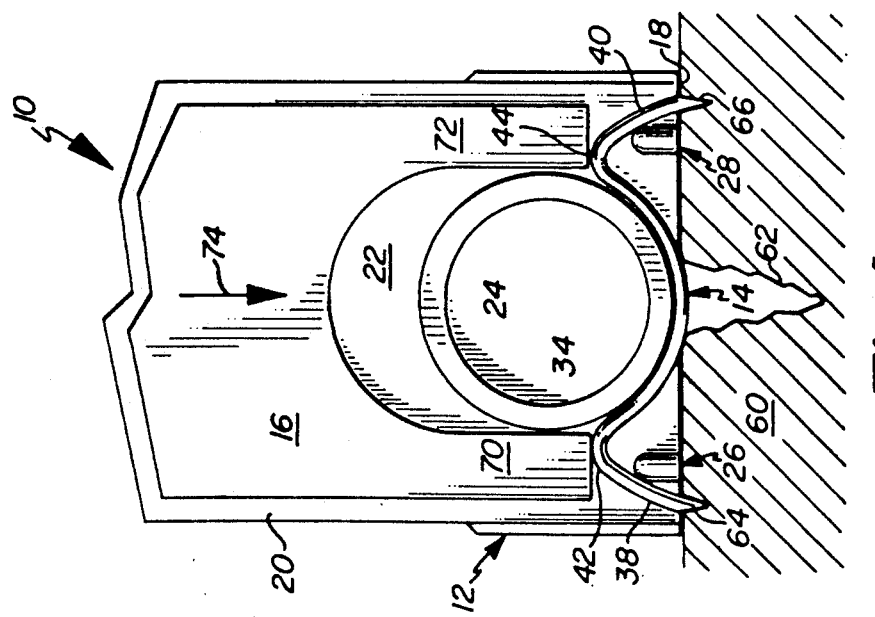

SURGICAL STAPLING INSTRUMENT

BACKGROUND OF THE INVENTION

The present invention relates to surgical stapling. More specifically, the invention relates to a surgical stapling instrument for use in microsurgery that stores a staple in a flexed and open state.

Surgical staples are well known in the art as fast and efficient wound closing devices. As such, they may either replace or complement retention sutures for joining adjacent body tissue. Typically, stapling instruments join adjacent body tissue by delivering a metal staple with a stapling gun. The stapling gun applies a mechanical force to permanently deform the staple from a generally U-shaped configuration to a final, closed configuration which holds the adjacent tissue together. Obviously, the force required to bend the staple must be applied at or adjacent the staple application site. As a result, these prior art staple guns require the positioning of relatively large and bulky mechanisms at the staple application site to produce and apply the required bending force to the staple.

Wound closure requires precise positioning of each staple to reduce tissue trauma, minimize blood loss, and achieve optimum cosmetic results. However, large, bulky staple guns are clumsy to control and reduce the accuracy with which a surgeon can position each staple. Further, since the bending force is required at the site of application, the necessary bulk of the gun at the staple application site limits the use of staples in many instances where their use would be otherwise desirable.

Hall et al U.S. Pat. No. 4,396,139 discloses a surgical staple gun that reduces the overall size and weight of the staple gun in order to provide more exacting control for the surgeon. The staple gun disclosed in Hall stores a plurality of resilient staples, each in a relaxed closed configuration. During delivery, a staple is flexed into an open crescent shape, and is released to return to its closed configuration while simultaneously piercing and drawing together adjacent edges of body tissue. The force required to flex each staple is much less than the force required to permanently deform the metal staples of the prior art. The overall size and weight of the staple gun can therefore be reduced.

However, the staple gun of Hall still requires a mechanical force near the tip of the gun (at the application site of the staple) to flex and release each staple. As a result, the staple gun is still large and clumsy. Further, the ejected staple tends to pinch the adjacent body tissue together, rather than holding the tissue together evenly while allowing the tissue to heal. Also, the expansion pins of Hall must be extricated after the staple is "closed" in the tissue.

Staple guns of the prior art are effective for rejoining a wide variety of tissue types and bones, such as the rib cage, fascia, muscle, skin and fat. These staple guns, however, are ineffective for use in microsurgery. Microsurgery applications include ophthalmology, otolaryngolical, neural, vascular, and intervascular surgery, among others. In cataract surgery, for example, the size of the staple may be two millimeters or less and must penetrate a distance less than one millimeter to avoid piercing the eyeball. Such small staples limit the use of clamping and bending tools. Further, the bulk of any conceivable bending tool limits accessibility in cases where surgery must be performed through very small and/or relatively deep openings.

SUMMARY OF THE INVENTION

The present invention provides a surgical stapling instrument that is effective for stapling body tissue in microsurgery. The stapling instrument does not perform a mechanical bending or deliver a flexing force near its tip during insertion of the staple into body tissue. The absence of bending and flexing tools at the staple application site allows an overall instrument size (dimension and length) that is suitable for microsurgery.

The surgical stapling instrument of the present invention includes a staple, a retainer, and a plunger. The staple is preformed in a closed state and is made of a body-compatible material. The staple material either undergoes elastic deformation or has a plateau in its stress vs. strain curve such that the staple may be flexed to an open state without permanent deformation. The retainer stores the staple in the open state while the plunger acts to eject the staple from the retainer such that the staple returns itself to the preformed closed state at a desired application site.

In a preferred embodiment, the staple includes a pair of legs, each extending from the instrument and terminating at a penetrating tip. When closing a wound, a surgeon accurately places the instrument across adjacent body issue to be joined and presses the penetrating tips into the body tissue. The surgeon then releases the staple with the plunger and the staple returns itself to the preformed closed state to thereby join the adjacent body tissue.

BRIEF DESCRIPTION OF THE DRAWINGS

FIG. 1 is a perspective view of a surgical stapling instrument in accordance with the present invention.

FIG. 2 is a plan view of a flexible staple in accordance with the present invention in a preformed closed state.

FIG. 3 is a plan view of the staple of FIG. 2 which illustrates a range of flexure.

FIGS. 4 and 5 are sectional views of torn body tissue which illustrate a process of applying a staple to the body tissue in accordance with the present invention.

FIG. 6 is a plan view of an alternative embodiment of a stapling instrument in accordance with the present invention.

FIG. 7 is a sectional view of the instrument of FIG. 6 taken along line 7—7.

DETAILED DESCRIPTION OF THE PREFERRED EMBODIMENTS

The present invention provides a surgical stapling instrument that is effective for use in microsurgery. FIG. 1 is a perspective view of a surgical stapling instrument 10 in accordance with the present invention. The instrument 10 includes a retainer 12, a staple 14 and a plunger 16. The retainer 12 includes a handle 20 that supports a tray 22. The tray 22 includes a stub 24, a pair of stops 26 and 28, a first retaining wall 30, and a second retaining wall 32. The stub 24 is formed from the tray 22 and has a generally curved wall 34.

The retainer 12 holds the staple 14 near a discharge end 18 in a "loaded" state—ready for application. During application, the surgeon holds the instrument 10 by the handle 20 and presses the discharge end 18 of the retainer 12 against the body tissue to be joined. As will be described more fully below, the staple will penetrate the body tissue to be joined while still in the retainer 12.

The surgeon then urges the plunger 16 against the staple 14 to release the staple with the self-straightening of the staple 14 driving the staple 14 into the body tissue. The instrument 10 holds a single staple that is preloaded during manufacture. After a single use, the surgeon may discard the retainer 12.

The staple 14 is preformed in a closed state (see FIG. 2). However, the retainer 12 stores the staple 14 in a flexed and generally open state. The staple 14 includes a yoke 36, a first leg 38, and a second leg 40. The staple 14 sits on the tray 22 with each stop 26 and 28 engaging one of the staple legs 38 and 40 to press the yoke 36 against the curved wall 34 with enough force to flex the yoke and bias the staple 14 into a generally open state. In essence, the staple 14 is "loaded" onto the tray 22 and confined in the loaded position in any desired manner—as by a sheath as discussed below.

As shown in FIG. 2, the yoke 18 of staple 14 includes a first shoulder 42 and a second shoulder 44. The first leg 38 extends from the first shoulder 42 in a first arc 46. The second leg 40 extends from the second shoulder 44 in a second arc 48. The first and second legs 38 and 40 are coplanar with the yoke 36.

The staple 14 is preferably made from an elastic material or a metal having a large plateau in its stress vs. strain curve ("stress plateau"). That is, if the yoke 36 is elastically flexed or flexed from an original position (the preformed, closed position) without permanent deformation to a flexed position that is within the stress plateau, the yoke will return itself to the original position, on release of the flexing force. If the yoke 36 is flexed beyond the end of the stress plateau, it will not return itself to the original position. Accordingly, material selection for the staple 14 is significant in the practice of the present invention.

FIG. 3 is a plan view of the staple 14 illustrating a range of flexure within the stress plateau. The yoke 36 may be flexed between a preformed closed state 50 and a flexed and open state 52 without permanent deformation. The retainer 12 stores the staple 14 in the flexed and open state 52 so that when the plunger 20 ejects the staple, it will return itself to the closed state 50. This "return" is generally along the arcs designated 46 and 48. That is, the first and second legs 38 and 40, remain coincident with the first and second arcs 46 and 48, respectively, during ejection. The staple legs 38 and 40 therefore create a clean and neat closure in the closed state 50, rather than pinching or pulling the tissue. Guides 30' and 32', which may be a portion of the walls 30 and 32 in the embodiment of FIG. 1, for example, may be provided to maintain the movement of the legs 38 and 40 along the arcs 46 and 48, respectively or such other paths as may be desired.

FIGS. 4 and 5 are sectional views of a surgical incision 62 in body tissue 60 and illustrate a process of applying the staple 14 to the body tissue. The surgical stapling instrument 10 includes the retainer 12, the staple 14, and the plunger 16. In a preferred embodiment, the legs 38 and 40 extend beyond the discharge end 18 of the retainer 12 in the loaded position. This allows the surgeon to precisely position the staple 14 over a wound 62 and to penetrate the tissue 60 with the legs 38 and 40 prior to releasing the staple. The staple legs 38 and 40 preferably terminate in penetrating tips 64 and 66, respectively, to facilitate this penetrating. The tips 64 and 66 reduce the force required to pierce the tissue 60 and may be of any known design.

The plunger 16 includes tabs 70 and 72 that engage the shoulders 42 and 44 of the staple 14 for releasing the staple out of the discharge end 18 and into the tissue 60. In a preferred embodiment, the stops 26 and 28 are ramps. When the surgeon slides the plunger 16 with a given force 74, the tabs 70 and 72 engage the shoulders 42 and 44 and push the staple 14 up and over the ramps of stops 26 and 28 to eject the staple and release it from the instrument 10

FIG. 5 illustrates the staple 14 fully installed in the tissue 60. The staple 14 has returned itself to the original closed state. The tissue 60 is now secured by the staple 14.

Scar formation is a major concern for surgeons when closing wounds. The human body reacts to foreign bodies and cause the body's defense mechanisms to seal them off with corrective tissue. When the body's reaction is greater, more scar tissue will be formed. Therefore, the staple 14 is preferably made from a body-compatible material.

In the preferred embodiment, the staple 14 is made from a metal alloy called Nitinol. Nitinol is an alloy of approximately 50% nickel and 50% titanium. Nitinol is particularly suited for the present application since it is both body-compatible and capable of considerable flexure without permanent deformation—that is, it has a large stress plateau. It should be known that a variety of other materials having similar characteristics may also be used. In some applications, a superior plastic may be used for staple material.

The overall size and dimensions of the retainer and the staple may be varied for specific applications. In cataract surgery, for example, the size of the staple should have a yoke that is less than 2 millimeters across, and should have legs that penetrate less than 1 millimeter to avoid piercing the eyeball. The dimensions of the retainer can be scaled accordingly.

In other applications, surgery must be performed through a very small access hole. The present invention is uniquely suited for this type of application. The stapling instrument may be formed with a long, narrow retainer that will pass through the small access hole.

FIGS. 6 and 7 illustrate an alternative embodiment of the stapling instrument of the present invention. FIG. 6 is a plan view of a stapling instrument 80. The instrument 80 includes a retainer 82, a staple 84, and a plunger 86. The retainer 82 includes a handle 88 and a tray 90. A stub 92 and a pair of stops 94 and 96 are formed in the tray 90. The tray 90 does not include retaining walls, such as the retaining walls 30 and 32 shown in FIG. 1. The retaining walls are replaced with a sheath 98 which is wrapped around the tray 90. The sheath 98 holds both the staple 84 and the plunger 86 to the tray 90.

FIG. 7 is a sectional view of the instrument 80 taken along line 7—7 of FIG. 6. The instrument 90 includes the staple 84, the plunger 86, the tray 90, the stub 92, the stop 94, and the sheath 98. It is likely that a sheath such as that shown at 98 will be necessary to retain the staple in the embodiments of FIG. 1.

In another alternative embodiment (not shown), the tray 22 shown in FIGS. 1, 4 and 5 may also be wrapped in a sheath, such as sheath 98 shown in FIGS. 6 and 7. The stapling instrument of the present invention is designed for a single use. The instrument is preferably made from a relatively inexpensive material, such as plastic. During manufacture, the instrument is formed, loaded with a staple, and sealed in a sterile container for delivery.

The present invention provides a surgical stapling instrument that is small, light, and easy for surgeons to handle. Further, the present invention is particularly effective for microsurgery where stapling instruments were previously too large and clumsy to be effective.

Although the present invention has been described with reference to preferred embodiments, workers skilled in the art will recognize that changes may be made in form and detail without departing from the spirit and scope of the invention.

What is claimed is:

1. An instrument for stapling body tissue, comprising:
   staple means preformed in a closed state and made of a body-compatible material having a stress plateau such that the staple means may be flexed to an open state without permanent deformation;
   means for storing the staple means in the open state, the storing means having a discharge end and further comprising means for retaining the staple means within the storing means in the open state; and
   means for ejecting the staple from the retaining means at the storing means discharge end such that the staple returns itself to the performed closed state.

2. The instrument of claim 1 wherein the staple means comprises:
   a yoke having a first shoulder and a second shoulder;
   a first leg extending in a first arc from the first shoulder; and
   a second leg extending in a second arc from the second shoulder, the first and second legs and the yoke being coplanar.

3. The instrument of claim 2 wherein the yoke is substantially straight and the first and second legs have a generally closed form in the closed state.

4. The instrument of claim 3 wherein the first and second legs travel generally along the first and second arcs when moving from the open state to the closed state.

5. The instrument of claim 2 wherein the first and second legs each terminate at a penetrating tip.

6. The instrument of claim 1 wherein the staple means is made from a metallic alloy comprising approximately 50 percent nickel and 50 percent titanium.

7. The instrument of claim 1 wherein the staple means is made from a plastic.

8. The instrument of claim 1 wherein the staple means has first and second legs, at least one of the staple means legs extending past the storing means discharge end.

9. The instrument of claim 8 wherein the ejecting means comprises plunger means movable toward the discharge end for urging the staple means from the discharge end.

10. The instrument of claim 1 wherein the ejecting means comprises plunger means movable toward the discharge end for urging the staple means from the discharge end.

11. An instrument of stapling body tissue comprising:
    staple means preformed in a closed state and made of a body-compatible material having a stress plateau such that the staple means may be flexed to an open state without permanent deformation, the staple means further comprising:
    a yoke having a first shoulder and a second shoulder;
    a first leg extending in a first arc from the first shoulder; and
    a second leg extending in the second arc from the second shoulder, the first and second legs and the yoke being "planar";
    retainer means for storing the staple means in the open state, the retainer means comprising:
    a handle;
    a tray coupled to the handle and having a generally planar surface with a discharge end;
    a stub formed in the tray near the discharge end and having a generally curved wall; and
    a pair of stops formed in the tray, the stops being positioned about the stub and generally adjacent the discharge end with each stop engaging one of the first and second staple legs to press the yoke against the curved wall for storing the staple means in the open state; and
    means for ejecting the staple from the retainer means such that the staple returns itself to the preformed closed state.

12. The instrument of claim 11 wherein the tray includes first and second retaining wall extending from the discharge end such that the first staple leg is positioned between the first wall and one of the stops and the second staple leg is positioned between the second wall and the other stop.

13. The instrument of claim 12 wherein the first and second staple legs extend past the discharge end.

14. The instrument of claim 12 wherein the stub, the stops, and the first and second retaining walls hold the first and second staple legs coincident with the first and second arcs before and during ejection.

15. The instrument of claim 12 wherein the means for ejecting comprises a plunger extending along the handle and including first and second tabs that are slidably positioned between the first wall and the stub and between the second wall and the stub, respectively, the first and second tabs engaging the staple means at the first and second shoulders.

16. The instrument of claim 15 and further comprising a sheath wrapped around the tray, the staple means and the plunger for holding the staple means and the plunger on the tray.

17. The instrument of claim 11 wherein the stops form a pair of ramps that hold the staple means in the open state while facilitating release of the staple means from the instrument by the means for ejecting.

18. The instrument of claim 17 wherein the means for ejecting comprises a plunger movable between a store position and an eject position, whereby moving the plunger from the store position to the eject position forces the staple over the stop ramps and ejects the staple means from the discharge end such that the staple means returns itself to the preformed closed state.

* * * * *